US009863873B2

(12) United States Patent
Brown et al.

(10) Patent No.: US 9,863,873 B2
(45) Date of Patent: Jan. 9, 2018

(54) INFRARED SPECTROMETER MEASUREMENT OF DROPLETS COLLECTED FROM AN OIL MIST IN A BREATHER PIPE OF A GAS TURBINE

(71) Applicant: Siemens Aktiengesellschaft, Munich (DE)

(72) Inventors: Roger Brown, Middlesex (GB); Robert Pearce, Wickenby (GB)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/385,640

(22) PCT Filed: Mar. 12, 2013

(86) PCT No.: PCT/EP2013/054961
§ 371 (c)(1),
(2) Date: Sep. 16, 2014

(87) PCT Pub. No.: WO2013/143835
PCT Pub. Date: Oct. 3, 2013

(65) Prior Publication Data
US 2015/0076352 A1 Mar. 19, 2015

(30) Foreign Application Priority Data
Mar. 27, 2012 (EP) ..................... 12161510

(51) Int. Cl.
*G01N 21/3504* (2014.01)
*G01N 1/20* (2006.01)
(Continued)

(52) U.S. Cl.
CPC ......... *G01N 21/3504* (2013.01); *F01D 21/10* (2013.01); *F01M 11/10* (2013.01);
(Continued)

(58) Field of Classification Search
CPC ............ G01N 21/3504; G01N 21/274; G01N 21/3554
(Continued)

(56) References Cited

U.S. PATENT DOCUMENTS 4,045,671 A * 8/1977 Dille et al. ................. 250/341.1
4,164,653 A * 8/1979 Matumoto et al. ........... 250/301
(Continued)

FOREIGN PATENT DOCUMENTS

CN 1668909 A 9/2005
CN 102052075 A 5/2011
(Continued)

OTHER PUBLICATIONS

JP 2002-350339 translation.*
(Continued)

*Primary Examiner* — David Porta
*Assistant Examiner* — Djura Malevic
(74) *Attorney, Agent, or Firm* — Beusse Wolter Sanks & Maire

(57) ABSTRACT

A method for analyzing a droplet fraction of an oil mist sample of a gas turbine is provided. A collecting device collects the oil mist sample, wherein the collecting device is arranged within a breather pipe which is coupled to the gas turbine such that oil mist is flowing through the breather pipe. The droplet fraction is separated from a gaseous fraction of the oil mist sample by a filter device, wherein the filter device is soaked with the droplet fraction, the droplet fraction is extracted from the filter device by using a tetrachloroethylene solvent. A composition of the droplet fraction is analyzed by a spectrometer.

20 Claims, 2 Drawing Sheets

(51) Int. Cl.

| | | |
|---|---|---|
| *G01N 1/22* | (2006.01) | |
| *F01M 11/10* | (2006.01) | |
| *F01D 21/10* | (2006.01) | |
| *F16N 7/32* | (2006.01) | |
| *G01N 21/27* | (2006.01) | |
| *G01N 21/3554* | (2014.01) | |
| G01N 33/28 | (2006.01) | |
| F01M 13/00 | (2006.01) | |
| B01D 11/02 | (2006.01) | |

(52) U.S. Cl.
CPC ............. *F16N 7/32* (2013.01); *G01N 1/2035* (2013.01); *G01N 1/2205* (2013.01); *G01N 21/274* (2013.01); *G01N 21/3554* (2013.01); B01D 11/02 (2013.01); F01M 13/00 (2013.01); F16N 2250/50 (2013.01); G01N 33/2888 (2013.01)

(58) Field of Classification Search
USPC ........... 250/339.09, 301, 492.1, 343, 339.07, 250/338.5, 339.1, 574
See application file for complete search history.

(56) References Cited

U.S. PATENT DOCUMENTS

| | | | | |
|---|---|---|---|---|
| 4,213,044 | A | * | 7/1980 | Perrotta .................. 250/301 |
| 4,624,133 | A | * | 11/1986 | Iwashita .................. 73/61.43 |
| 4,687,327 | A | | 8/1987 | Wheeless |
| 5,301,536 | A | | 4/1994 | Fernandez et al. |
| 5,750,999 | A | * | 5/1998 | Fox ......................... 250/343 |
| H001757 | H | | 11/1998 | Seltzer |
| 5,974,860 | A | * | 11/1999 | Kuroda et al. ............... 73/40 |
| 6,369,890 | B1 | * | 4/2002 | Harley .................... 356/337 |
| 6,455,851 | B1 | | 9/2002 | Lord et al. |
| 7,748,280 | B2 | | 7/2010 | Jaffe et al. |
| 8,256,307 | B2 | | 9/2012 | Graze, Jr. et al. |
| 2002/0166365 | A1 | | 11/2002 | Kogure et al. |
| 2002/0178729 | A1 | * | 12/2002 | Care et al. ................... 60/772 |
| 2005/0087027 | A1 | | 4/2005 | Widmer |
| 2005/0160838 | A1 | | 7/2005 | Weaver |
| 2005/0241481 | A1 | | 11/2005 | Honda et al. |
| 2006/0242933 | A1 | * | 11/2006 | Webb et al. .................. 55/486 |
| 2007/0039373 | A1 | * | 2/2007 | Hoflinger et al. ............. 73/23.2 |
| 2008/0156073 | A1 | | 7/2008 | Borjon et al. |
| 2009/0211370 | A1 | | 8/2009 | Ferri et al. |
| 2010/0145634 | A1 | | 6/2010 | Pinguet et al. |
| 2014/0026583 | A1 | * | 1/2014 | Care .................. B64C 1/1453 60/772 |
| 2015/0041653 | A1 | | 2/2015 | Brown et al. |

FOREIGN PATENT DOCUMENTS

| | | |
|---|---|---|
| DE | 19704461 C1 | 5/1998 |
| DE | 102006026002 A | 12/2007 |
| EP | 1528385 A1 | 5/2005 |
| EP | 1757927 A2 | 2/2007 |
| EP | 1936358 A1 | 6/2008 |
| EP | 2831558 A1 | 2/2015 |
| GB | 2269675 A | 2/1994 |
| GB | 2350195 A | 11/2000 |
| GB | 2398382 A | 8/2004 |
| GB | 2408798 A | 6/2005 |
| GB | 2432425 A | 5/2007 |
| GB | 2447908 A | 10/2008 |
| JP | 2002350339 A | 12/2002 |
| JP | 2004219131 A | 8/2004 |
| JP | 2005164408 A | 6/2005 |
| JP | 2008157648 A | 7/2008 |
| RU | 2330263 C2 | 7/2008 |
| RU | 79181 U1 | 12/2008 |
| RU | 2446389 C2 | 3/2012 |
| SU | 239920 A1 | 3/1969 |
| WO | 2013143756 A1 | 10/2013 |

OTHER PUBLICATIONS

Suuroonen K. et al; "Respiratory Exposure to Components of Water-Miscible Metalworking Fluids";The Annals of Occupational Hygiene, LNKD-PUBMED: 18678881; vol. 52. No. 7, pp. 607-614; ISSN: 1475-3162; XP002681978; Oct. 7, 2008.

Asikainen V. et al; "Mineral oil residues on HVAC components: measuring methods"; Building and Environment Aug. 2003 Elsevier Ltd; vol. 38, No. 8, pp. 1057-1061; DOI: DOI:10.1016/S0360-1323(03)00059-3; XP002681977; 2008; GB; Aug. 8, 2008.

"Oil Mist in Textile Workplace Atmospheres (FREON 113)" Occupational Safety & Health Administration, 200 Constitution Avenue, NW Washington, DC 20210, www.osha.gov.

Aniruddha Pisal "Determination of Oil and Grease in Water with a Mid-Infrared Spectrometer" PerkinElmer, Inc. Shelton, CT 06484 USA; 2009.

"InfraCal Model CVH" http://wilksir.com/oilgrease-analyzers/infracal-cvh.

Peter M. Eller et al "NIOSH Manual of Analytical Methods" 4th Edition, US Department of Health and Human Services; pp. A15-A29, Aug. 1994.

Asikainen V. et al; "Mineral oil residues on HVAC components: measuring methods"; Building and Environment Aug. 2003 Elsevier Ltd; vol. 38, No. 8, pp. 1057-1061; DOI: DOI:10.1016/S0360-1323(03)00059-3; XP002681977; 2008; GB; Aug. 8, 2008 (Previously Cited).

Susan Michaelis; Contaminated aircraft cabin air, BRC, Milestone House, Journal of Biological Physics and Chemistry 11, pp. 132-145, DOI: 10.4024/24M111A.jbpe.11.04, 2011.

* cited by examiner

INFRARED SPECTROMETER MEASUREMENT OF DROPLETS COLLECTED FROM AN OIL MIST IN A BREATHER PIPE OF A GAS TURBINE

CROSS REFERENCE TO RELATED APPLICATIONS

This application is the U.S. National Stage of International Application No. PCT/EP2013/054961 filed Mar. 12, 2013, and claims the benefit thereof. The International Application claims the benefit of European Application No. EP12161510 filed Mar. 27, 2012. All of the applications are incorporated by reference herein in their entirety.

FIELD OF INVENTION

The present invention s to a method for analysing a droplet fraction of an oil mist sample of a gas turbine and to a system for analysing a droplet fraction of an oil mist sample of a gas turbine.

ART BACKGROUND

In the technical field of gas turbines there is a commercial requirement to measure the emissions from gas turbine engines in order to comply with national and regional environmental standards. In particular, there is a need to measure lube oil breather emissions from a gas turbine. The lube oil breather emission flows through a breather pipe in a liquid (droplet) and/or a gaseous aggregate state. The lube oil breather pipe comprises a relatively small diameter and the flow of the lube oil (mist) is relatively low and comprises high temperatures.

Hence, in order to receive a proper measurement result, a measurement sample has to be taken from the oil mist inside breather pipe. In particular, the hydrocarbon amount of the oil mist in the gaseous phase and in the liquid phase is measured, so that a total amount of hydrocarbon of the oil mist and hence the lube oil breather emissions is analysed.

GB 2 408 798 A discloses a light scattering oil mist detecting device with means for preventing oil droplets entering the casing. The oil mist detecting device comprises a casing having an oil mist introducing chamber arranged in a crank-case of on internal combustion engine. A light emitting means and a photo detecting means of the oil mist detecting device may measure the oil mist introduced into the introducing chamber.

GB 2 398 382 A discloses an oil mist sampling device. The oil mist sampling device comprises light emitting means for radiating light and photo receiving means for receiving the radiated light. The photo receiving means outputs a signal corresponding to the intensity of the received light.

U.S. Pat. No. 6,369,890 B1 discloses a particle separation and detection apparatus. The apparatus comprises an analysing chamber which receives a gaseous fluid by diffusion from a receiving chamber connected via an inlet to an area being monitored. The gaseous fluid is measured by a photodiode which detects light scattered by particles in the gaseous fluid.

EP 1 936 358 A1 discloses an oil mist detector. A light emit-ting device irradiates light to a detection region in which oil mist is injected. The light is radiated through a transparent window. The received light is received through the transparent window by a receiving device.

Liquid emissions may be caught on a fiber packed filter assembly with a backup membrane filter. A conventional method of determining the liquid oil catch is weighting before and after exposure but this may be prone to possible errors. The more accurate method may be to extract the liquid oil catch from an exhausted oil mist by using a solvent and then analyzing the concentration of the liquid oil catch (e.g. its hydrocarbons) in the solvent.

SUMMARY OF THE INVENTION

It may be an object of the present invention to provide a proper analyzing method for an oil mist emission of a gas turbine.

This object may be solved by a method for analyzing a droplet fraction of an oil mist sample of a gas turbine and by a sys-tern for analyzing a droplet fraction of an oil mist sample of a gas turbine according to the independent claims.

According to a first aspect of the present invention, a method for analyzing a droplet fraction of an oil mist sample of a gas turbine is presented. According to the method, the oil mist sample is collected by a collecting device. The collecting device is arranged within a breather pipe which is coupled to the gas turbine such that oil mist is flowing through the breather pipe. The droplet fraction is separated from a gaseous fraction of the oil mist sample by a filter device, such that the filter device is soaked with the droplet fraction. The droplet fraction is extracted from the filter device by using tetrachloroethylene as the solvent. The droplet fraction, mixed with the tetrachloroethylene solvent, is analyzed by a spectrometer, for example by an infrared spectrometer.

According to a further aspect of the present invention a system for analyzing a droplet fraction of an oil mist sample of a gas turbine is presented. The system comprises a collecting device for collecting the oil mist sample, a filter device and spectrometer, for example an infrared spectrometer. The collecting device is arranged within the breather pipe which is coupled to the gas turbine such that oil mist is flowed through the breather pipe. The filter device is adapted for separating the droplet fraction from the gaseous fraction of the oil mist sample such that the filter device is soaked with the droplet fraction. The spectrometer is adapted for analyzing a composition of the droplet fraction which is ex-tractable from the filter device by using tetrachloroethylene as the solvent.

The breather pipe is connected for example to a bearing housing of a gas turbine which provides a bearing of the shaft of the gas turbine or any other device (e.g. combustion engines) with an oil breather. Bearings of the gas turbine are lubricated generally with lube oil, for example. Due to high temperatures during operation of a gas turbine, oil mist may be generated. The oil mist comprises the oil in a first fraction, i.e. in a gaseous aggregate state, and in a second fraction, i.e. in a liquid/droplet aggregate state. The oil mist flows through the breather pipe e.g. to a collecting tank. The breather pipe may comprise a circular, elliptical or rectangular cross-sectional cross section.

There is a need to measure the composition of the oil mist, which is exhausted through the breather pipe. In particular, there is a need to analyse the composition of the oil mist due to environmental requirements. Furthermore, the composition of the oil mist may provide information about certain defects of a gas turbine and defects of a bearing of the gas turbine, respectively.

The collecting device collects a sample of the oil mist. For example, the respective collecting device may collect the respective sample and forward the collected sample, i.e. the liquid and/or gaseous fraction, of the oil mist sample to an external analysing unit which may be located outside of the breather pipe. Specifically, the collecting device may comprise a respective opening section through which the sample of the oil mist may enter the respective collecting device. Furthermore, the collecting device may comprise a suction unit or may be connected to a suction unit, such that the sample may be sucked into a respective inner volume of the collecting device with a predefined velocity in order to generate an isokinetic flow of the fluid when entering the opening section. The collecting device comprises an inner volume and an opening section through which the respective sample of the fluid is entered from the breather pipe into the inner volume. The opening section may be detachably fixed to the respective collecting device. Hence, the respective oil mist sample may enter the inner volume of the respective collecting device through the respective opening section. Inside the inner volume e.g. the filter device and/or analysing units, such as the optical analysing device (e.g. the spectrometer, may be installed.

The filter device may comprise for example quartz/glass wool and/or a filter membrane in order to separate the first fraction (liquid, droplet fraction) and the second fraction (gaseous fraction) from the collected sample.

The spectrometer may be arranged externally with respect to the breather pipe, for example in an adjacent laboratory. By the spectrometer, a composition of the droplet (liquid) fraction of the collected sample is analyzed. After extraction of the droplet fraction from the filter device, the droplet fraction is mixed with the tetrachloroethylene solvent. The spectrometer analyses and measures the mixture of the droplet fraction and the tetrachloroethylene solvent. In particular, the amount of gaseous species, methane only hydrocarbons (MOHC) of carbon monoxide (CO), of carbon dioxide ($CO_2$) and of total hydrocarbons (THC) of the droplet fraction may be analyzed. Furthermore, the amount of the extracted droplet fraction of the sample is measurable by the infrared spectrometer.

Furthermore, the infrared spectrometer is calibrated in order to achieve proper measurement results. The infrared spectrometer measures in particular the solution of the droplet fraction of the oil mist sample and the tetrachloroethylene solvent by measuring the absorption of the radiated light (e.g. infrared light).

By the present invention, the droplet fraction is extracted from the filter device by using a tetrachloroethylene solvent. Tetrachloroethylene ($C12C=CC12$) is in particular a solvent for dissolving organic materials, such as the oil droplets which are absorbed by the filter device. In Conventional approaches, flammable and highly polluting solvents, such as Freon, are used. According to the approach of the present invention, tetrachloroethylene is used which is highly stable and non-flammable. Furthermore, tetrachloroethylene is less pollutant to the environment and less toxic in comparison to other previously used solvents, such as Freon. Furthermore, the tetrachloroethylene solvent is qualified for the use in spectroscopy analysis, i.e. infrared spectroscopy analysis. Hence, by the present invention, an analyzing method is presented which is less dangerous for the environment and for the whole analyzing procedure.

The droplet fraction of the oil mist which is gathered in the filter device may be extracted by the tetrachloroethylene solvent by using e.g. a Soxhlet extractor. By using the Soxhlet extractor, it may be assured that most of the collected droplet fraction of the oil mist is extractable from the filter device (e.g. the quartz wool) together with the tetrachloroethylene solvent.

The extracted droplet fraction together with the tetrachloroethylene solvent is analyzed by the (infrared) spectrometer.

According to a further exemplary embodiment, the separating of the droplet fraction from a gaseous fraction of the oil mist comprises the separating of the droplet fraction from a gaseous fraction of the oil mist by using a wool element, in particular a quartz wool element.

The filter device, i.e. the wool element, which is soaked with the droplet fraction of the oil mist may be put into the Soxhlet device, which may be used as an extracting device. In the extracting device the tetrachloroethylene solvent which is used for the extraction separates the droplet fraction of the oil mist sample from the filter device.

According to a further exemplary embodiment, the filter device is arranged within the collecting device, in particular inside the inner volume of the collecting device. Hence, during operation of the gas turbine, no further external attachment equipment, such as connecting lines or other attachments therein, are necessary to be connected to the breather pipe.

Hence, the separation of the droplet fraction from the gaseous fraction of the oil mist sample is accomplished directly inside the collecting device. Hence, the gas turbine may be operated continuously, such that during the operation time the filter device separates continuously the gathered and collected droplet fraction of the oil mist sample.

On predefined servicing periods, the collecting device and/or the filter device may be taken out of the breather pipe and the filter device may be put into the extracting unit, such as the Soxhlet device. The collecting device may be set up with another filter device while the taken out filter device is still in the Soxhlet device. Hence, the maintenance time of the gas turbine is reduced due to the exchangeable filter device within the collecting device.

According to a further exemplary embodiment of the method, after separating the droplet fraction from a gaseous fraction, of the oil mist, the gas fraction is guided to a ous fraction analyzing unit by a connecting line, which connects the collecting device with the gaseous fraction analyzing unit. Hence, the gaseous fraction may be guided continuously during operation of the gas turbine to the gaseous fraction analyzing unit and the gaseous fraction, so that the composition of the gaseous fraction may be analyzed during operation of the gas turbine.

The gaseous fraction of the respective sample may be measured by a flame ionization detector (FID). By the flame ionization detector in particular a volatile organic compounds (VOC), such as hydrocarbons, in a composition of the respective sample may be measured. A flame ionization detector is based on the measuring of the conductivity of a flame gaseous fluid between two electrodes, wherein hydrogen is used as a burnable gas and which is mixed together with the gas fraction of the fluid. In this process electrons are released which get caught by a surrounding metallic wire. This results in a changed conductivity so that the composition of the gas fraction may be determined.

In an exemplary embodiment, a first collecting device and a second collecting device are arranged within the breather pipe. The first collecting device and/or the second collecting device is connected by a respective connection line to an external device, such as the gaseous analysing unit, the filter device or the extraction device. Inside the respective inner volume, the filter device is arrangeable for separating the gaseous fraction from the liquid/droplet fraction of the respective oil mist sample. The gaseous fraction is guided through the connection line to the external gaseous analyzing device. The liquid fraction is gathered within the e.g. glass wool of the filter device. After a predetermined time of collecting the sample inside the respective collecting device, the soaked glass wool may be taken out of the respective collecting device. In a laboratory, the liquid fraction is separated from the glass wool and the amount and the composition of the liquid fraction are analysed. Hence, the liquid droplet fraction may be measured offline (e.g. when the analysing arrangement is not inside the breather pipe) in a laboratory whilst the gas analysis may be performed continuously online (e.g. when the analysing arrangement is located inside the breather pipe and the engine, e.g. the gas turbine, is operating).

The connection line may comprise a length of approximately 5 m to approximately 25 m (meters), particularly 15 m to 20 m, such that the gaseous fraction may be analysed in a safe distance with respect to the breather pipe. Furthermore, the connecting line may be trace heated, e.g. a heating element, a heating braid or a heating jacket, in order to keep the temperature and hence the fluid flow characteristic of the gaseous fraction to be analysed approximately unchanged. Hence, unbiased analysing results even spaced apart from the breather pipe may be achieved.

According to an exemplary embodiment of the method, the velocity, the pressure and/or the temperature of the fluid flowing through the breather pipe is measured. Hence, the flow characteristics of the fluid inside the breather pipe may be determined such that for example an isokinetic sample collection is adjustable.

In particular, according to an exemplary embodiment of the method, a diameter of an opening section of at least one of the first collecting devices and the second collecting devices are adjusted depending on the measured velocity, the measured pressure and/or the measured temperature of the fluid flowing through the breather pipe such that the fluid flows in an isokinetic manner through the opening into an inner volume of the respective first collecting device or the respective second collecting device.

Furthermore, the first collecting device and the second collecting device may be attached to a spool piece, wherein the spool piece may be detachably arranged to e.g. a flange of the breather pipe. This analysing arrangement comprising the spool piece and the respective collecting devices may be installed at different breather pipes e.g. from different gas turbines, wherein the analysing arrangement may be adjusted to the individual flow conditions of the fluid flowing through a respective breather pipe. By adjusting the diameter of the opening of the respective collecting device, the measurement adjustment may be adapted to different operating conditions so that an isokinetic flow through the opening is provided even at various operating conditions.

Hence, the analysing arrangement may be detachably mounted to a breather pipe, such that the analysing arrangement may be used for different breather pipes of e.g. different gas turbines.

It has to be noted that embodiments of the invention have been described with reference to different subject matters. In particular, some embodiments have been described with reference to apparatus type claims whereas other embodiments have been described with reference to method type claims. However, a person skilled in the art will gather from the above and the following description that, unless otherwise notified, in addition to any combination of features belonging to one type of subject matter also any combination between features relating to different subject matters, in particular between features of the apparatus type claims and features of the method type claims is considered as to be disclosed with this application.

BRIEF DESCRIPTION OF THE DRAWINGS

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

DETAILED DESCRIPTION

Figure 1:
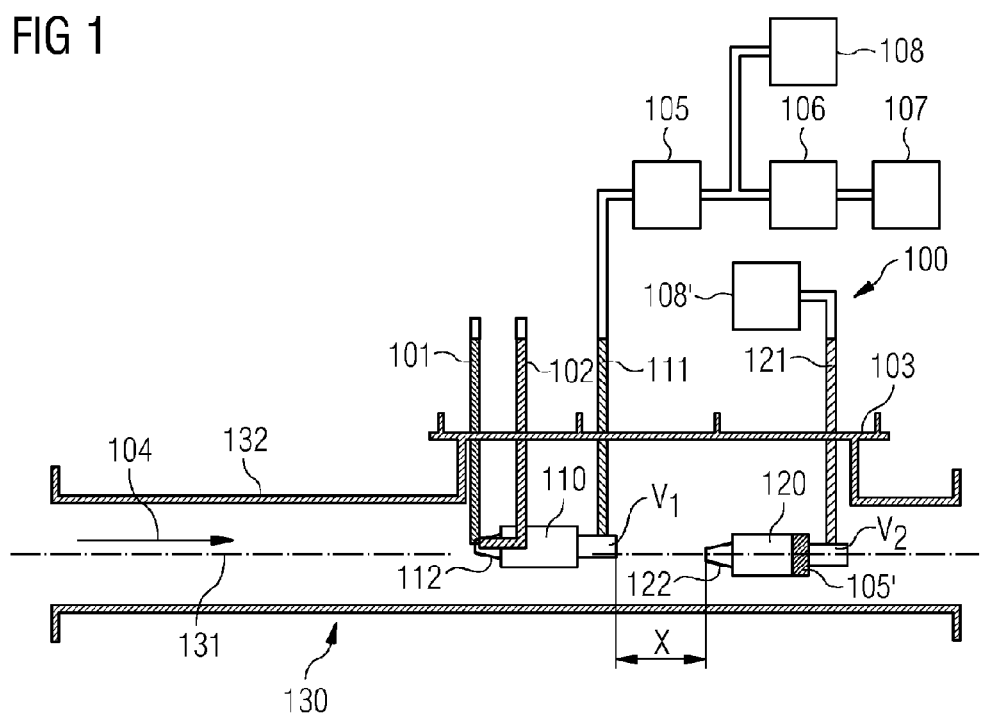
FIG. 1 shows an exemplary embodiment of a system for analyzing a droplet fraction of an oil mist sample of a gas turbine according to an exemplary embodiment of a present invention.

The illustrations in the drawings are schematical. It is noted that in different figures, similar or identical elements are provided with the same reference signs.

FIG. 1 shows a system 100 for analyzing a droplet fraction of an oil mist sample of a gas turbine according to an exemplary embodiment of the present invention. The system 100 comprises a collecting device 110; 120 for collecting the oil mist sample. The collecting device 110; 120 is arranged within a breather pipe 130 which is coupled to the gas turbine such that at least a part of the oil mist is flowed through the breather pipe 130. Furthermore, a filter device 105 is shown, which separates the droplet/liquid fraction of the oil mist from a gaseous fraction of the oil mist, wherein the filter device 105, 105' is soaked with the droplet fraction of the oil mist. The filter device 105, 105' may be an external filter device 105 which is arranged outside of the breather pipe 130 or an internal filter device 105' which is installed inside an inner volume VI, V2 of a respective collecting device 110; 120.

Furthermore, an (e.g. infrared) spectrometer 107 is arranged externally to the breather pipe 130 for analyzing a composition of the droplet fraction which is extractable from the filter device 105, 105' by using a tetrachloroethylene solvent.

The system 100 in FIG. 1 comprises two collecting devices 110; 120, in particular a first collecting device 110 and a second collecting device 120, which are arranged inside the breather pipe 130 such that the oil mist has at the leading edge (upstream edge) of the first collecting device 110 and at the leading edge (upstream edge) of the second collecting device 120 the same flow characteristics.

The breather pipe 130 comprises a centre axis 131 which may be for example the symmetry axis of the breather pipe 130. The centre axis 131 is surrounded by the pipe wall 132. The first collecting device 110 comprises a first opening section 112 through which the sample of the fluid flowing through the breather pipe 130 may enter the first collecting device 110. The first oil mist sample may flow further to an inner volume VI of the first collecting device 110.

From the inner volume VI, the oil mist sample may be guided by a first connection line to an externally arranged filter device 105, which is located outside of the breather pipe 130.

As exemplary shown in FIG. 1, in the second inner volume V2 of the second collecting device 120 the internal filter device 105' may be arranged, such that the second oil mist sample which is collected by the second collecting device 120 may be separated into a droplet (liquid) fraction and a gaseous fraction. The gaseous fraction of the second oil mist sample may be guided through a second connection line 121 to a gaseous fraction analysing unit 108'. The internal filter device 105' may be taken out of the breather pipe 130 after a predetermined operation time of the gas turbine and may be put into the extracting device 106.

Figure 3:
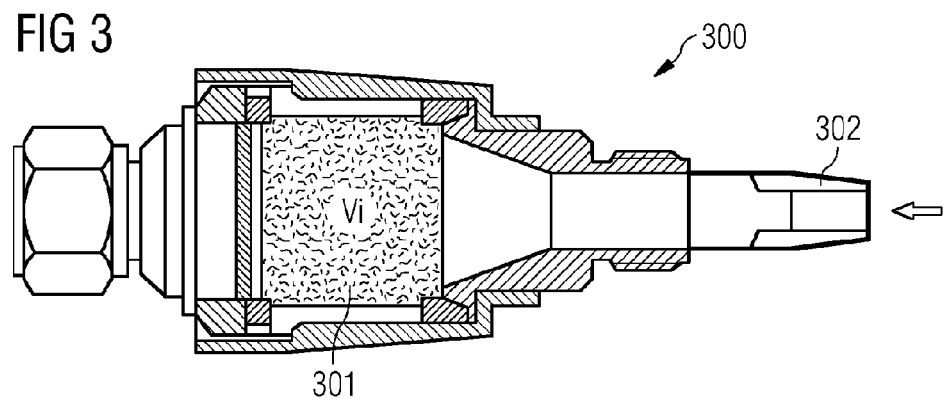
FIG. 3 shows an exemplary embodiment of a collecting device according to an exemplary embodiment of the present invention.

The filter device 105, 105' may comprise a wool element 301, for example (see FIG. 3).

As can be taken from the first collecting device 110, a thermometer 101 (e.g. a resistance thermometer or a thermocouple) and a pressure gauge 102 may be attached, such that the flow characteristics of the fluid and/or the first sample may be measured.

The opening section 112 of the first collecting device 110 comprises an opening with a predefined diameter such that the fluid is flowable into the inner volume VI. Furthermore, the opening section 112 may form a nozzle type section which may be detachably mounted to a body of the first collecting device 110. As can be taken from FIG. 1, the opening section 112 may comprise a wedge-shape in order to improve the aerodynamic profile of the first collecting device 110.

Furthermore, the second collecting device 120 may be arranged with a predefined axial offset x along the centre axis 131 with respect to the first collecting device 110. Hence, by providing a predefined offset x between both collecting devices 110, 120 the turbulences of the fluid which passes the first collecting device 110 may be reduced such that at a downstream located second opening section 122 of the second collecting device 120 an almost laminar and undisturbed flow of the fluids inside the breather pipe 130 is achieved again. Hence, the fluid characteristics and parameters at the first opening section 112 are identical to the flow parameters of the fluid at the second opening section 122. Hence, a more precise extraction and analysing of the first oil mist sample and the second oil mist sample are achieved.

Furthermore, as can be taken from FIG. 1, the first collecting device 110 and the second collecting device 120 may be attached to a spool piece 103, wherein the spool piece 103 may be detachably arranged to e.g. a flange of the breather pipe 130. Hence, the spool piece 103 together with the first collecting device 110 and the second collecting device 120 may be used for a plurality of different breather pipes 130. Hence, a flexible analysing arrangement 100 may be provided.

The spool piece 103 may have a length along the axial direction along the centre line 131 of approximately 350 mm to approximately 450 mm (millimeters). Each of the first collecting device 110 and the second collecting device 120 may have a length along the axial direction of approximately 110 mm to approximately 130 mm. The offset x between the trailing edge (downstream end) of the first collecting device 110 and the leading edge (upstream end) of the second collecting device 120 may be approximately 90 mm to approximately 110 mm. The breather pipe 130 may have a diameter of approximately 90 mm to approximately 110. Specifically, the offset x may have approximately the same value as the diameter of the breather pipe 130. The dimensions given above may vary depending on the size of the gas turbine.

Figure 2:
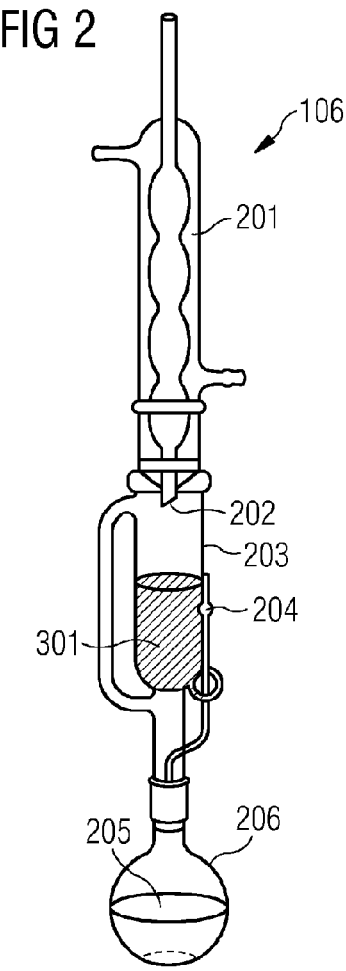
FIG. 2 shows an exemplary embodiment of a Soxhlet device.

After separating the droplet fraction from a gaseous fraction by the filter device 105, the filter device 105 is put into an extracting device 106 and the gaseous fraction is guided to a gaseous analyzing unit 108, 108'. The extraction device 106 may comprise a Soxhlet device as shown in FIG. 2. The droplet fraction of the oil mist is extracted from the filter device 105, 105' by using tetrachloroethylene solvent. The mixture of the droplet fraction of the oil mist and the tetrachloroethylene solvent is then analyzed by an e.g. infrared spectrometer 107. In particular, the composition of the droplet device, such as the total hydrogen carbon of the droplet fraction, is analyzed. Moreover, the weight of the collected droplet fraction of the oil mist is measured by the infrared spectrometer.

In FIG. 2, the separating unit 106, which is exemplary a Soxhlet device, is shown. The soaked filter device 105, 105', which may be in particular a soaked wool element 301, is put into a thimble 203 of the Soxhlet device. In a boiling flask 206 the extraction solvent 205, in particular the tetrachloroethylene solvent, is filled. The extraction solvent 205 is heated up and evaporates. The extraction solvent vapour moves up to a condenser 201, where the extraction solvent condensates again. The condensed extraction solvent drops in an extraction chamber 202 and the thimble 203, respectively.

The droplets of the extraction solvent 205 solve the droplet oil mist fraction from the wool element 301. If the mixture consisting of the extraction solvent 205 and the droplet fraction of the oil mist reaches a predetermined height in-side the extraction chamber 202, the mixture of extraction solvent 205 and oil mist droplet flows back in the boiling flask 206. In the boiling flask 206, the mixture of extraction solvent 205 and the droplet fraction of the oil mist are gathered. If the extraction solvent 205 has solved all of the liquid droplet fraction of the oil mist from the wool element 301, the mixture consisting of the extraction solvent 205 and the droplet fraction is provided to the spectrometer 107 (e.g. the infrared spectrometer) for analyzing the composition of the droplet fraction of the oil mist.

FIG. 3 shows an exemplary embodiment of a collecting device 300. The collecting device 300 may be installed in the breather pipe 130 for the first collecting device 110 or for the second collecting device 120. As can be taken from FIG. 3, the collecting device 300 comprises an opening section 302 which may be detachably mounted to the collecting device 300. The input flow direction is indicated by the arrow in FIG. 3. The collecting device 300 shows a wool element 301 which is installed inside the inner volume Vi of the collecting device 300. The wool element 301 may be part of the filter device unit 105. The wool element 301 may be made of a quartz or glass wool such that the liquid part of the respective sample may be separated and gathered in the wool element 301.

It should be noted that the term "comprising" does not exclude other elements or steps and "a" or "an" does not exclude a plurality. Also elements described in association with different embodiments may be combined. It should also be noted that reference signs in the claims should not be construed as limiting the scope of the claims.

The invention claimed is:

1. A method for analysing a droplet fraction of an oil mist sample of a gas turbine, the method comprising:
   collecting the oil mist sample by a collecting device, wherein the collecting device is arranged within a breather pipe which is coupled to the gas turbine such that oil mist is flowing through the breather pipe, separating the droplet fraction from a gaseous fraction of the oil mist sample by a filter device, wherein the filter device is soaked with the droplet fraction, extracting the droplet fraction from the filter device by using a tetrachloroethylene solvent, and analysing a composition of the droplet fraction by a spectrometer.

2. The method according to claim 1, wherein the spectrometer is an infrared spectrometer.

3. The method according to claim 1, wherein the separating of the droplet fraction from the gaseous fraction of the oil mist sample is carried out by means of a wool element of the filter device; and wherein the filter device is arranged within the collecting device.

4. The method according to claim 3, further comprising after separating the droplet fraction from a gaseous fraction of the oil mist sample, guiding the gaseous fraction by a connecting line to a gaseous fraction analysing unit.

5. The method of claim 3, wherein the separating of the droplet fraction from the gaseous fraction of the oil mist sample is carried out by means of a quartz wool element of the filter device.

6. The method according to claim 1, wherein the filter device is arranged within the collecting device.

7. The method of claim 6, further comprising:

removing the filter device from the collecting device;

positioning the filter device in a separating unit to perform the extracting of the droplet fraction from the filter device; and placing another filter device in the collecting device during the extracting step.

8. The method according to claim 1, further comprising calibrating the infrared spectrometer.

9. The method of claim 1, wherein the extracting the droplet fraction from the filter device comprises:

positioning the filter device in a separating unit; and combining the tetrachloroethylene solvent and the filter device within the separating unit to form the composition of the droplet fraction.

10. The method of claim 9, wherein the combining the tetrachloroethylene solvent and the filter device comprises:

evaporating the tetrachloroethylene solvent; and condensing the tetrachloroethylene solvent with a condenser into a chamber of the separating unit housing the filter device.

11. The method of claim 9, further comprising collecting the composition of the droplet fraction in a flask of the separating unit including directing a flow of the composition into the flask when a level of the composition within the separating unit reaches a predetermined height.

12. The method of claim 1, wherein the filter device is arranged within the breather pipe.

13. The method of claim 1, further comprising:

measuring at least one of a temperature, a pressure and a velocity of the oil mist flowing within the breather pipe; and adjusting a diameter of an opening section of the collecting device based on the measuring step, such that an isokinetic flow of the oil mist enters the opening section.

14. The method of claim 1, further comprising guiding the gaseous fraction of the oil mist sample to a gaseous fraction analyzing unit to solely determine the gaseous fraction of the oil mist sample.

15. A system for analysing a droplet fraction of an oil mist sample of a gas turbine, the system comprising:

a collecting device for collecting the oil mist sample, wherein the collecting device is arrangeable within a breather pipe which is coupleable to the gas turbine such that oil mist is flowable through the breather pipe, a filter device for separating the droplet fraction from a gaseous fraction of the oil mist sample, wherein the filter device is soaked with the droplet fraction, and a spectrometer for analysing a composition of the droplet fraction which is extractable from the filter device by using a tetrachloroethylene solvent.

16. The system of claim 15, further comprising a Soxhlet extractor to extract the droplet fraction from the filter device with the tetrachloroethylene solvent.

17. The system of claim 15, wherein the collecting device is positioned within the breather pipe and includes an internal filter device positioned within the collecting device.

18. The system of claim 15, including a pair of collecting devices positioned within the breather pipe, said pair of collecting devices arranged with a predefined axial offset along a center axis of the breather pipe such that fluid characteristics of the oil mist at a respective opening section of the collecting devices is substantially identical.

19. A method for analysing a droplet fraction of an oil mist sample of a gas turbine, the method comprising:

collecting the oil mist sample by a collecting device, wherein the collecting device is arranged within a breather pipe which is coupled to the gas turbine such that oil mist is flowing through the breather pipe, separating the droplet fraction from a gaseous fraction of the oil mist sample by a filter device, wherein the filter device is soaked with the droplet fraction, extracting the droplet fraction from the filter device by using a non-flammable solvent, and analysing a composition of the droplet fraction by a spectrometer.

20. The method of claim 19, wherein the extracting the droplet fraction from the filter device comprises:

positioning the filter device in a separating unit;

combining the solvent and the filter device within the separating unit to form the composition of the droplet fraction; and collecting the composition of the droplet fraction in a flask of the separating unit.

\* \* \* \* \*